United States Patent
Yoo et al.

(10) Patent No.: US 12,253,505 B2
(45) Date of Patent: Mar. 18, 2025

(54) CONTACT COMBUSTION TYPE HYDROGEN SENSOR AND METHOD FOR MANUFACTURING SAME

(71) Applicants: Hyundai Motor Company, Seoul (KR); Kia Corporation, Seoul (KR)

(72) Inventors: Il Seon Yoo, Suwon-si (KR); Hyun Soo Kim, Yongin-si (KR); Jang Hyeon Lee, Gunpo-si (KR); Dong Gu Kim, Suwon-si (KR); Dae Sung Kwon, Seoul (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 225 days.

(21) Appl. No.: 17/742,659

(22) Filed: May 12, 2022

(65) Prior Publication Data
US 2023/0034945 A1 Feb. 2, 2023

(30) Foreign Application Priority Data
Jul. 29, 2021 (KR) .......................... 10-2021-0100188

(51) Int. Cl.
G01N 33/00 (2006.01)
G01N 27/16 (2006.01)

(52) U.S. Cl.
CPC ........... *G01N 33/005* (2013.01); *G01N 27/16* (2013.01)

(58) Field of Classification Search
CPC .............................. G01N 27/16; G01N 33/005
See application file for complete search history.

(56) References Cited

U.S. PATENT DOCUMENTS

| | | | |
|---|---|---|---|
| 5,451,371 A * | 9/1995 | Zanini-Fisher | G01N 27/16 431/89 |
| 7,791,150 B1 | 9/2010 | Seal et al. | |
| 9,261,472 B2 * | 2/2016 | Kimura | G01N 25/4873 |
| 10,017,379 B2 | 7/2018 | Rajaraman et al. | |
| 2010/0170888 A1 * | 7/2010 | Lee | G01N 27/128 374/152 |

FOREIGN PATENT DOCUMENTS

| | | | | |
|---|---|---|---|---|
| CN | 106153221 A * | 11/2016 | | G01L 1/18 |
| JP | 4686922 B2 * | 5/2011 | | |
| JP | 2019056605 A | 4/2019 | | |
| JP | 6679788 B1 | 4/2020 | | |
| JP | 6679789 B1 | 4/2020 | | |
| KR | 100905106 B1 | 6/2009 | | |
| KR | 20100026810 A | 3/2010 | | |
| WO | WO-2019111463 A1 * | 6/2019 | | G01F 1/68 |

* cited by examiner

*Primary Examiner* — Justin N Olamit
(74) *Attorney, Agent, or Firm* — Slater Matsil, LLP (57) ABSTRACT

An embodiment contact combustion type hydrogen sensor includes a substrate including silicon, lamination layers disposed over a top surface of the substrate and including a first thin oxide layer and a first thin nitride layer, a heater over the lamination layers, the heater including a connecting part electrically connected to a predetermined part and a heating part configured to be heated in response to power being applied, insulating layers covering a top surface of the heater and configured to perform an insulating operation, the insulating layers including a second thin oxide layer and a second thin nitride layer, a platinum catalyst over the insulating layers and configured to be heated by the heater to perform a hydrogen reaction, and a slit outside the heating part and passing through the substrate and the lamination layers.

17 Claims, 7 Drawing Sheets

CONTACT COMBUSTION TYPE HYDROGEN SENSOR AND METHOD FOR MANUFACTURING SAME

CROSS-REFERENCE TO RELATED APPLICATIONS

This application claims the benefit of Korean Patent Application No. 10-2021-0100188, filed on Jul. 29, 2021, which application is hereby incorporated herein by reference.

TECHNICAL FIELD

The present disclosure relates to a contact combustion type hydrogen sensor and a method for manufacturing the same.

BACKGROUND

Currently, interest in hydrogen as an eco-friendly alternative energy is continuously increasing. Thus, research is being conducted to rapidly replace existing fossil fuels in various fields such as automobiles, fuel cells, and internal combustion engines, and related industries that are being researched and developed are also increasing. However, since hydrogen has the risk of leakage and explosion due to high diffusivity, it is essential to prepare measures for safety against hydrogen leakage. Therefore, safety measures are being prepared using various hydrogen sensors around a hydrogen storage facility and a hydrogen-related device, and research and development related to the hydrogen sensors are being actively conducted.

Generally, the hydrogen sensor is classified into a semiconductor type, a contact combustion type, a FET (field effect transistor) type, an electrolyte type (electrochemical type), an optical fiber type, a thermoelectric type, etc. depending on a detection method. Among them, the contact combustion type hydrogen sensor is provided with a heater, so it is stable in a change in external environment such as external temperature and humidity, and it is effective in selectivity and stability by using a platinum-group catalyst with high selectivity for hydrogen.

However, most of currently available contact combustion type hydrogen sensors are problematic in that the sensors are manufactured in a bead type, so they require a lot of power to operate, and most of the manufacturing processes are performed manually, so mass productivity is low. Further, some hydrogen sensors are manufactured using MEMS (micro electro mechanical system) manufacturing technology that uses a thick or thin film material instead of a bead-type material. However, these sensors are problematic in that they are expensive, require high power consumption, and are low in sensitivity, so improvement of the sensors is required.

The foregoing is intended merely to aid in the understanding of the background of the present disclosure, and is not intended to mean that the present disclosure falls within the purview of the related art that is already known to those skilled in the art.

SUMMARY

Accordingly, embodiments of the present disclosure have been made keeping in mind problems occurring in the related art, and an embodiment of the present disclosure provides a contact combustion type hydrogen sensor, in which a lamination layer, a heater, an insulating layer, and a platinum catalyst are stacked on a silicon substrate, and a slit is formed to extend to an outside of a heating part of the heater, thus providing a higher temperature and more uniform heat distribution when heat generated from the heater is transferred to the platinum catalyst.

Embodiments of the present disclosure provide a contact combustion type hydrogen sensor, including a silicon substrate, lamination layers disposed to cover a top of the silicon substrate and stacked in an order of a first thin oxide layer and a first thin nitride layer, a heater disposed on the lamination layers, and including a connecting part electrically connected to a predetermined part and a heating part operated to be heated when power is applied, insulating layers disposed to cover a top of the heater, performing an insulating operation, and stacked in an order of a second thin oxide layer and a second thin nitride layer, a platinum catalyst deposited on the insulating layers and heated by the heater to perform a hydrogen reaction, and a slit formed outside the heating part to pass through the silicon substrate and the lamination layers.

The slit may pass through the insulating layers along with the silicon substrate and the lamination layers.

The contact combustion type hydrogen sensor may further include a through groove formed in each of the insulating layers to pass to the connecting part of the heater, and a metal pad inserted into the through groove to input power from an external device.

The contact combustion type hydrogen sensor may further include an etch line marked on each of the insulating layers to extend along an outside of the heating part.

The heating part may be formed in a preset pattern.

The heating part may be formed such that an outer portion thereof is formed in a shape of a circle and a pattern is formed inside the circle.

The heater may be formed in a linear shape, and may include on each of opposite ends thereof a connecting part electrically connected to a predetermined part, and on a middle portion thereof a heating part.

The contact combustion type hydrogen sensor may further include a through hole vertically penetrating a lower portion of the heating part from the silicon substrate to the first thin oxide layer.

The platinum catalyst may be deposited on the heater through a MEMS batch process.

Embodiments of the present disclosure provide a method of manufacturing a contact combustion type hydrogen sensor, including forming lamination layers, including a first thin oxide layer and a first thin nitride layer, on a silicon substrate, depositing and patterning a heater, including a heating part and a connecting part, on the first thin nitride layer, forming insulating layers, stacked in an order of a second thin oxide layer and a second thin nitride layer, on the heater, depositing a platinum catalyst on the insulating layers, and forming a slit along an outside of the heating part.

The method may further include forming a through groove on the second thin oxide layer.

The method may further include depositing a metal pad connected to the connecting part after forming the through groove.

The method may further include annealing the heater after depositing the second thin oxide layer on the heater.

The method may further include polishing the silicon substrate and forming a through hole after forming the slit.

The contact combustion type hydrogen sensor according to embodiments of the present disclosure is advantageous in that a lamination layer, a heater, an insulating layer, and a platinum catalyst are stacked on a silicon substrate, and a slit is formed to extend to an outside of a heating part of the heater, thus providing a higher temperature and more uniform heat distribution when heat generated from the heater is transferred to the platinum catalyst, and making the catalytic action of the platinum catalyst more active.

Further, the slit eliminates residual stress generated in the silicon substrate, the lamination layer, the heater, and the insulating layer, thus preventing the contact combustion type hydrogen sensor from being damaged.

BRIEF DESCRIPTION OF THE DRAWINGS

The above and other objectives, features, and other advantages of embodiments of the present disclosure will be more clearly understood from the following detailed description when taken in conjunction with the accompanying drawings, in which.

DETAILED DESCRIPTION OF ILLUSTRATIVE EMBODIMENTS

Specific structural or functional descriptions in the embodiments of the present disclosure disclosed in this specification or application are only for description of the embodiments of the present disclosure. The descriptions should not be construed as being limited to the embodiments described in the specification or application.

Since the present disclosure may be embodied in many different forms, particular embodiments will be illustrated in the drawings and will be described in detail herein. However, it is to be understood that the present description is not intended to limit the present disclosure to those exemplary embodiments, and the present disclosure is intended to cover not only the exemplary embodiments, but also various alternatives, modifications, equivalents and other embodiments that fall within the spirit and scope of the present disclosure.

It will be understood that, although the terms "first", "second", etc. may be used herein to describe various elements, these elements should not be limited by these terms. These terms are only used to distinguish one element from another element. For instance, a first element discussed below could be termed a second element without departing from the teachings of the present disclosure. Similarly, the second element could also be termed the first element.

It will be understood that when an element is referred to as being "coupled" or "connected" to another element, it can be directly coupled or connected to the other element or intervening elements may be present therebetween. In contrast, it should be understood that when an element is referred to as being "directly coupled" or "directly connected" to another element, there are no intervening elements present. Other expressions that explain the relationship between elements, such as "between", "directly between", "adjacent to", or "directly adjacent to" should be construed in the same way.

The terminology used herein is for the purpose of describing particular embodiments only and is not intended to be limiting. In the present disclosure, the singular forms are intended to include the plural forms as well, unless the context clearly indicates otherwise. It will be further understood that the terms "comprise", "include", "have", etc. when used in this specification, specify the presence of stated features, integers, steps, operations, elements, components, and/or combinations thereof but do not preclude the presence or addition of one or more other features, integers, steps, operations, elements, components, and/or combinations thereof.

Unless otherwise defined, all terms including technical and scientific terms used herein have the same meaning as commonly understood by one of ordinary skill in the art to which the present disclosure belongs. It will be further understood that terms used herein should be interpreted as having a meaning that is consistent with their meaning in the context of this specification and the relevant art and will not be interpreted in an idealized or overly formal sense unless expressly so defined herein.

Hereinafter, preferred embodiments of the present disclosure will be described in detail with reference to the accompanying drawings. Like reference numerals denote like components throughout the drawings.

Figure 1:
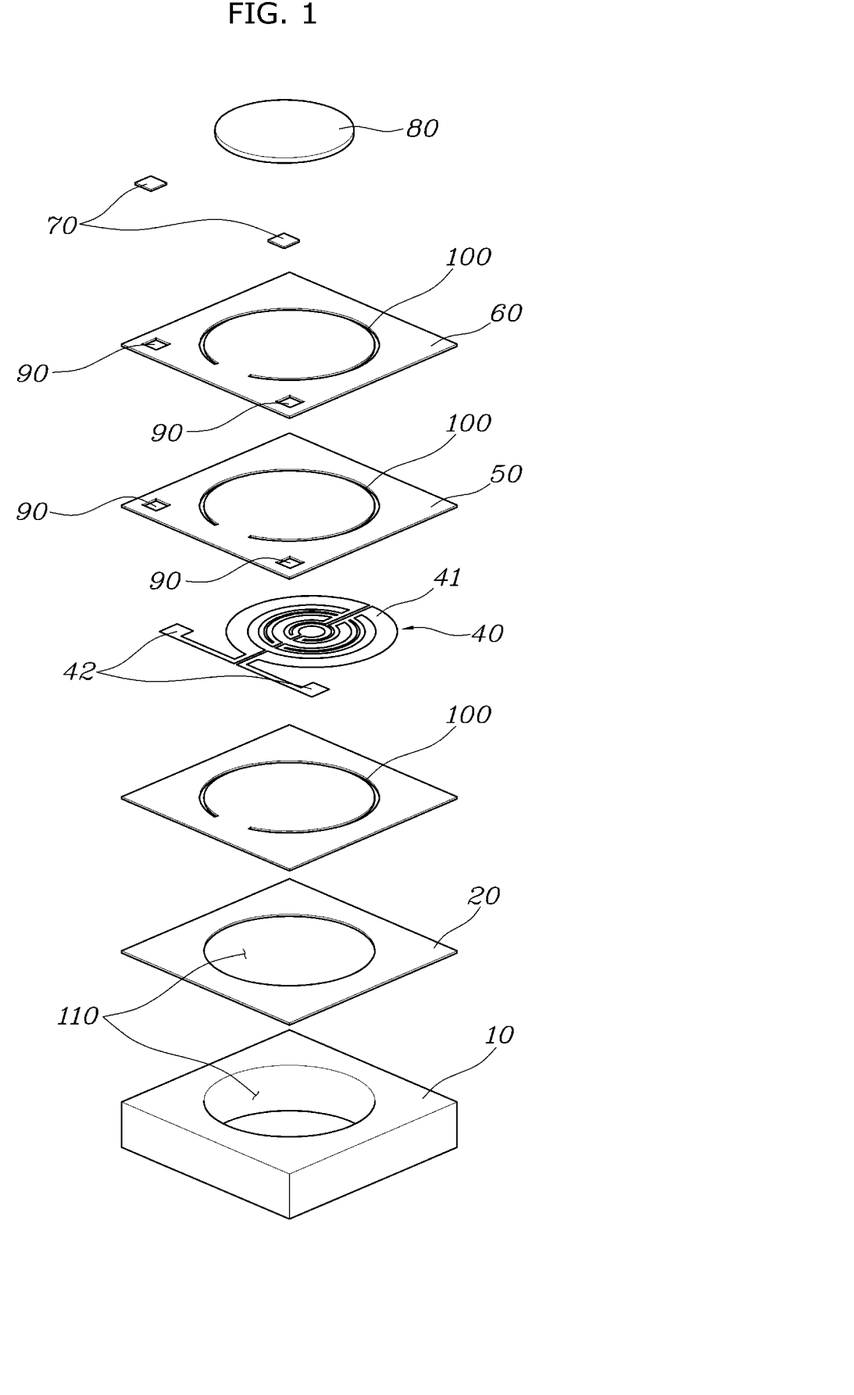
FIG. 1 is an exploded perspective view illustrating a contact combustion type hydrogen sensor according to an embodiment of the present disclosure.
Figure 2:
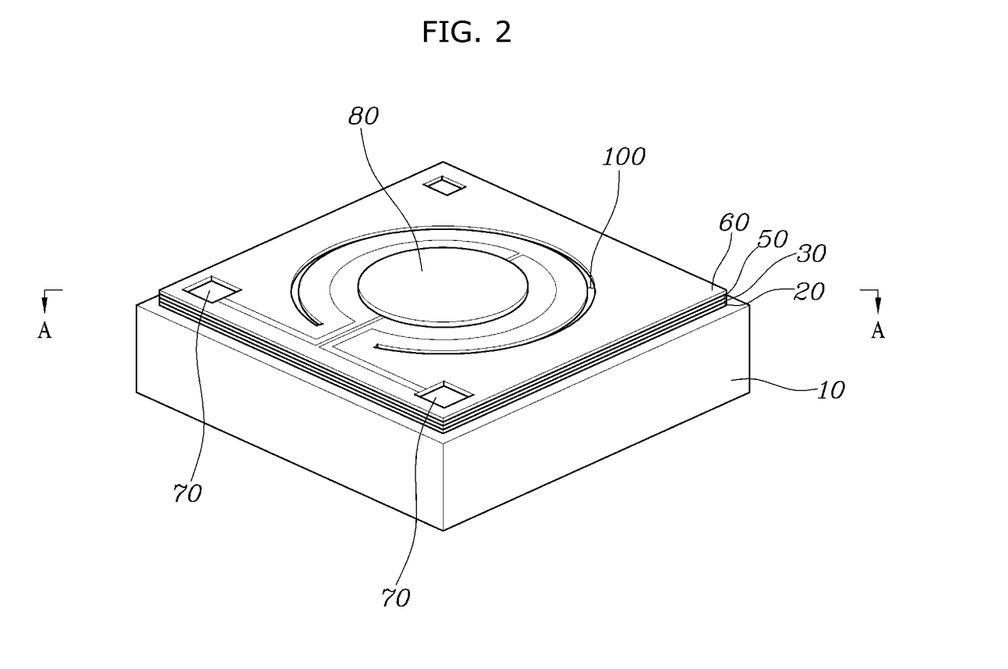
FIG. 2 is a perspective view illustrating the contact combustion type hydrogen sensor according to an embodiment of the present disclosure.
Figure 3:
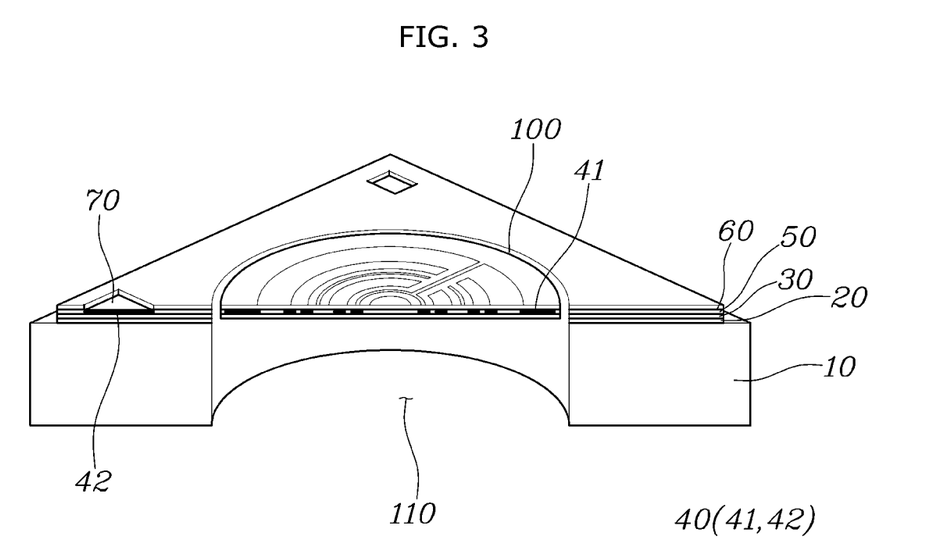
FIG. 3 is a sectional view taken along line A-A of FIG. 2.
Figure 4:
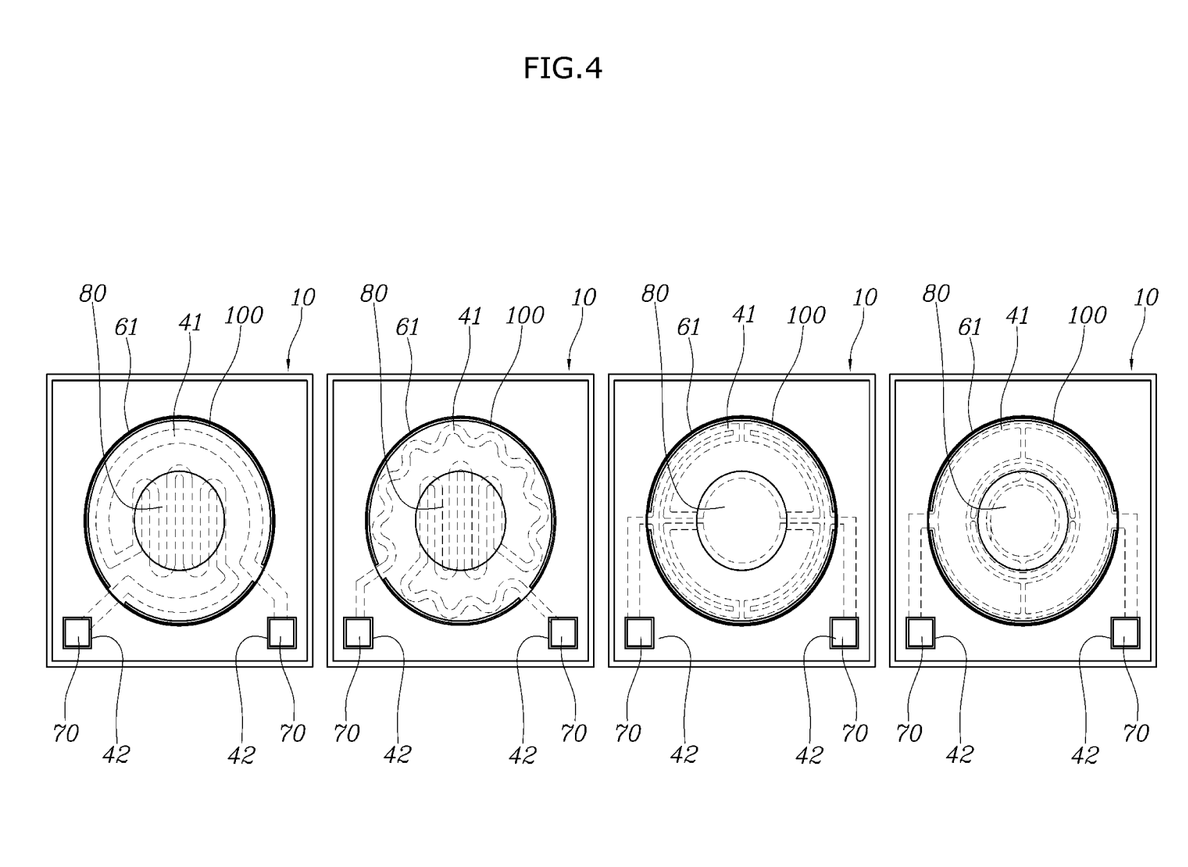
FIG. 4 is a plan view illustrating various patterns of a heating part of the contact combustion type hydrogen sensor according to an embodiment of the present disclosure.

FIG. 1 is an exploded perspective view illustrating a contact combustion type hydrogen sensor according to an embodiment of the present disclosure, FIG. 2 is a perspective view illustrating the contact combustion type hydrogen sensor according to an embodiment of the present disclosure, FIG. 3 is a sectional view taken along line A-A of FIG. 2, and FIG. 4 is a plan view illustrating various patterns of a heat part 41 of the contact combustion type hydrogen sensor according to an embodiment of the present disclosure.

The contact combustion type hydrogen sensor according to a preferred embodiment of the present disclosure will be described with reference to FIGS. 1 to 4.

First, the contact combustion type hydrogen sensor according to an embodiment of the present disclosure is configured to detect a local temperature difference due to heat generated from the oxidation reaction of hydrogen gas and a catalyst layer, and then measure the absolute concentration of the hydrogen gas from the detected temperature difference.

Thus, this is mounted on a device that uses hydrogen as fuel, like a hydrogen fueled vehicle, to detect the leakage of hydrogen and prevent an explosion from occurring due to the leakage of the hydrogen.

The contact combustion type hydrogen sensor according to an embodiment of the present disclosure includes a silicon substrate 10, lamination layers 20 and 30 disposed to cover a top of the silicon substrate 10 and stacked in the order of a first thin oxide layer 20 and a first thin nitride layer 30, a heater 40 disposed on the lamination layers 20 and 30 and including a connecting part 42 electrically connected to a predetermined part and a heating part 41 operated to be heated when power is applied, insulating layers 50 and 60 disposed to cover a top of the heater 40, performing an insulating operation, and stacked in the order of a second thin oxide layer 50 and a second thin nitride layer 60, a platinum catalyst 80 deposited on the insulating layers 50 and 60 and heated by the heater 40 to perform a hydrogen reaction, and a slit 100 formed outside the heating part 41 to pass through the silicon substrate 10 and the lamination layers 20 and 30.

As shown in FIGS. 1 to 4, the silicon substrate 10 may be provided, and the lamination layers 20 and 30 may be formed on the silicon substrate 10 and be composed of the first thin oxide layer 20 that is formed to cover the top of the silicon substrate 10 by applying an insulator, e.g., $SiO_2$ onto the silicon substrate 10 and the first thin nitride layer 30 formed to cover the top of the first thin oxide layer 20, thus protecting the silicon substrate 10. The first thin nitride layer 30 may be formed of $Si_3N_4$.

The heater 40 may be disposed on the lamination layers 20 and 30 to receive power from an external device and thereby generate heat. The heater 40 may be composed of the connecting part 42 that is electrically connected to the external device, and the heating part 41 that generates heat due to power input into the connecting part 42. The heater 40 may be formed of molybdenum (Mo).

The platinum catalyst 80 may be disposed on the insulating layers 50 and 60 by applying platinum (Pt), to react with hydrogen as the heating part 41 generates heat.

The slit 100 extends along the outside of the heating part 41 to pass through the lamination layers 20 and 30 and the silicon substrate 10, thus eliminating residual stress (compression) and thereby preventing the pattern resistance of the heater 40 from increasing, and improving heat distribution and thereby increasing thermal efficiency.

The external device applies power to the heater 40 through the connecting part 42, so current flows through the heater, and the platinum catalyst 80 may be deposited on the heating part 41 of the heater 40. In this case, the platinum catalyst 80 may interfere with the heating part 41 due to the current of the heating part.

Therefore, the insulating layers 50 and 60 composed of the second thin oxide layer 50 and the second thin nitride layer 60 may be formed to cover the top of the heater 40, and the platinum catalyst 80 may be deposited on the insulating layers 50 and 60 to be disposed on the heating part 41, thus transferring the heat of the heating part 41 and preventing electrical interference from occurring.

Further, the insulating layers 50 and 60 may prevent the heater 40 from being oxidized when the temperature of the heater rises due to heat generated by an applied voltage.

The slit 100 may pass through the insulating layers 50 and 60 along with the silicon substrate 10 and the lamination layers 20 and 30.

The slit 100 passing through the silicon substrate 10 and the lamination layers 20 and 30 may be formed to pass through the insulating layers 50 and 60 deposited on the lamination layers 20 and 30 and the heater 40.

This can simplify the process of manufacturing the slit 100, and can further enhance the effect of the slit 100 that eliminates the residual stress (compression) to prevent the pattern resistance of the heater 40 from increasing, and improves heat distribution to increase thermal efficiency.

Figure 5:
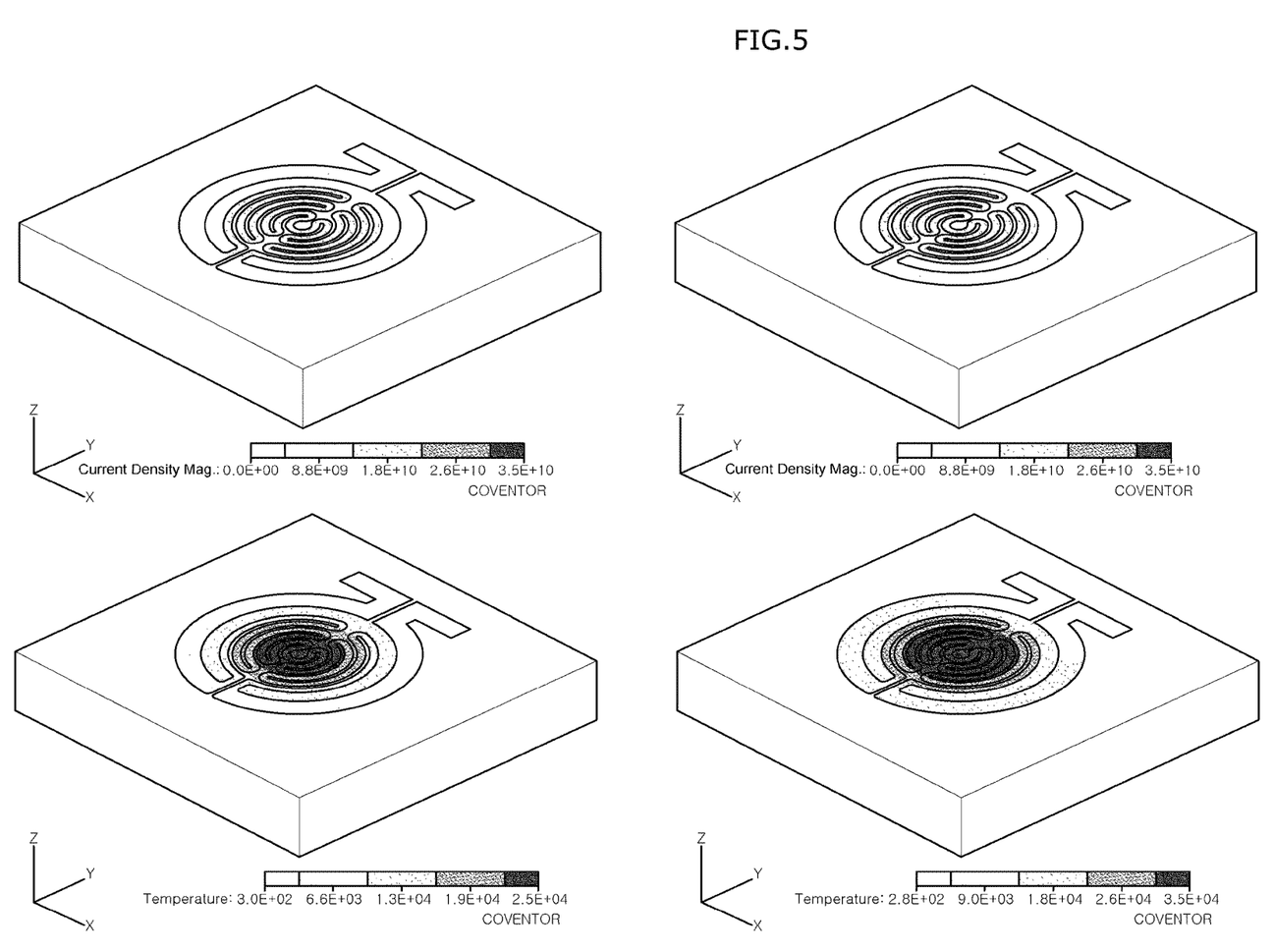
FIG. 5 is a heat distribution diagram of the contact combustion type hydrogen sensor according to an embodiment of the present disclosure, depending on whether there is a slit.

FIG. 5 is a heat distribution diagram of the contact combustion type hydrogen sensor according to an embodiment of the present disclosure, depending on whether there is the slit 100.

Referring to FIG. 5, the left diagram of FIG. 5 shows current density and temperature distribution in a state where the slit 100 is not formed, and the right diagram of FIG. 5 shows current density and temperature distribution in a state where the slit 100 is formed.

As shown in FIG. 5, the current distribution remains the same regardless of the presence or absence of the slit 100. However, as the slit 100 is formed through the silicon substrate 10, the lamination layers 20 and 30, and the insulating layers 50 and 60, this has the effect of having a higher temperature and more uniform heat distribution in the thin layer.

In embodiments of the present disclosure, the stresses of the first thin nitride layer 30, the first thin oxide layer 20, the second thin oxide layer 50, the second thin nitride layer 60, and the heater 40 may be designed, and the residual stress of the remaining components may be solved by the slit 100.

For example, the first thin oxide layer 20 may be set to −200 MPa, the first thin nitride layer 30 may be set to 10 MPa, the heater 40 may be set to 280 MPa, the second thin oxide layer 50 may be set to −210 MPa, the second thin nitride layer 60 may be set to 250 MPa, and the sum of the stresses may be 130 MPa. The residual stress may be 130 MPa, and the stress of 130 MPa may be solved by the slit 100, thus preventing the contact combustion type hydrogen sensor from being damaged.

Through grooves 90 passing to the connecting part 42 of the heater 40 may be formed in the insulating layers 50 and 60, and metal pads 70 may be inserted into the through grooves 90 to input power from an external device.

In order to connect the connecting part 42 of the heater 40 and the external power supply device, the through grooves 90 are formed in the insulating layers 50 and 60 to vertically communicate with each other and to be connected to the connecting part 42 of the heater 40, and the metal pads 70 connected to the connecting part 42 may be disposed in the through grooves 90.

The metal pads 70 allow the heater 40 to be easily connected to the external power supply device, and cause current to flow to the heater 40.

Etch lines may be marked on the insulating layers 50 and 60 to extend along the outside of the heating part 41.

The position of the heating part 41 of the heater 40 may not be easily recognized on the insulating layers 50 and 60. Thus, it is difficult to set the deposit position of the platinum catalyst, and the etch lines may be provided on the insulating layers 50 and 60 to be marked along the outer line of the heating part 41 so as to reduce the risk of burns due to the heat generated by the heating part 41.

Further, the position of the heating part 41 may be precisely recognized by etching the slit 100 along the etch line.

The heating part 41 may be formed in a preset pattern.

As shown in FIG. 4, the heating part 41 of the heater 40 may be formed in a preset pattern so as to have the maximum effect when emitting heat. The preset pattern may be variously formed.

The heating part 41 may be formed such that an outer portion thereof is formed in the shape of a circle and a pattern is formed inside the circle.

As shown in FIG. 4, the outer portion of the heating part 41 is formed in the shape of the circle to efficiently transmit heat to the circular platinum catalyst 80, and the preset pattern formed in the circle is set to cause current to flow through the heating part, thus generating heat through resistance.

The heater 40 may be formed in a linear shape, and may have on both ends thereof connecting parts 42 electrically connected to a predetermined part, and may have on a middle portion thereof a heating part 41.

The heater 40 may be made not by separately forming the heating part 41 and the connecting part 42 and then connecting the heating part and the connecting part, but by bending a middle portion of one electric wire to form the heating part 41 having the pattern in the circle and connecting both ends of the electric wire to positive and negative electrodes of the external power supply device such that power is applied to the heating part 41.

Therefore, this has the effect of improving convenience when manufacturing the heater 40 and reducing manufacturing cost.

The hydrogen sensor may further include a through hole 110 vertically penetrating a lower portion of the heating part 41 from the silicon substrate 10 to the first thin oxide layer 20.

As shown in FIGS. 1 and 3, a penetration part may be vertically formed in a lower portion of the silicon substrate 10 to be located under the heating part 41 of the heater 40, and the penetration part may pass through the silicon substrate 10 and the first thin oxide layer 20.

This allows heat generated from the heater 40 to escape to a bottom of the through hole 110, thus preventing the heat from damaging the silicon substrate 10, and allows necessary heat to be transferred to only a top, thus activating the platinum catalyst 80, and protecting the silicon substrate 10 located at a lower position.

The platinum catalyst 80 may be deposited on the heater 40 through a MEMS batch process.

The platinum catalyst 80 may be deposited on the heater 40 above the insulating layers 50 and 60 through the MEMS batch process. This has the effect of securing performance stability through the uniformity of the catalyst.

Figure 6:
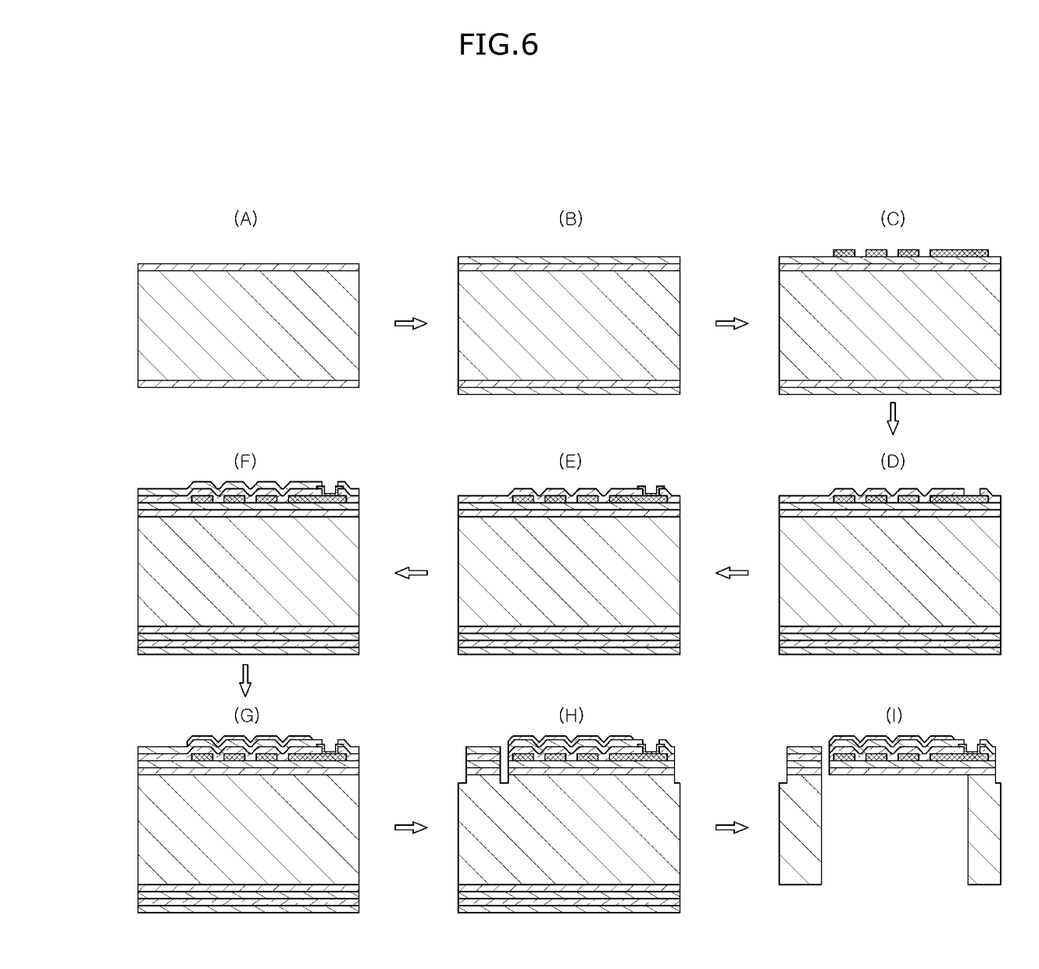
FIG. 6 is a sectional view illustrating a method of manufacturing a contact combustion type hydrogen sensor according to an embodiment of the present disclosure.
Figure 7:
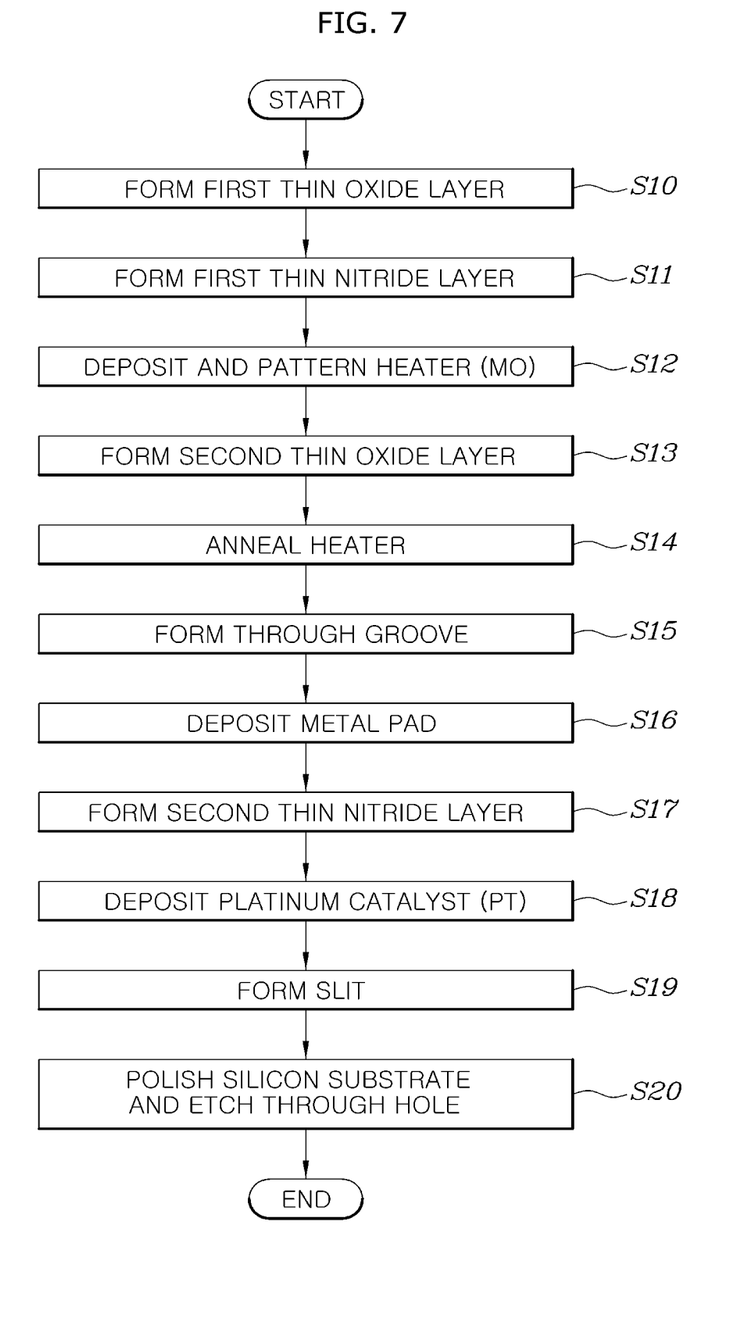
FIG. 7 is a flowchart illustrating a method of manufacturing the contact combustion type hydrogen sensor according to an embodiment of the present disclosure.

FIG. 6 is a sectional view illustrating a method of manufacturing a contact combustion type hydrogen sensor according to an embodiment of the present disclosure, and FIG. 7 is a flowchart illustrating a method of manufacturing the contact combustion type hydrogen sensor according to an embodiment of the present disclosure.

The method of manufacturing the contact combustion type hydrogen sensor according to a preferred embodiment of the present disclosure will be described with reference to FIGS. 6 and 7.

The method of manufacturing the contact combustion type hydrogen sensor according to an embodiment of the present disclosure includes steps S10 and S11 of forming lamination layers 20 and 30, including a first thin oxide layer 20 and a first thin nitride layer 30, on a silicon substrate 10, a step S12 of depositing and patterning a heater 40, including a heating part 41 and a connecting part 42, on the first thin nitride layer 30, steps S13 and S17 of forming the insulating layers 50 and 60, stacked in an order of a second thin oxide layer 50 and a second thin nitride layer 60, on the heater 40, a step S18 of depositing a platinum catalyst 80 on the insulating layers 50 and 60, and a step S19 of forming a slit 100 along an outside of the heating part 41.

The method may further include a step S15 of forming a through groove 90 in the second thin oxide layer 50.

After the step S15 of forming the through groove 90, the method may further include a step S16 of depositing a metal pad 70 connected to the connecting part 42.

After the step S13 of depositing the second thin oxide layer on the heater 40, the method may further include a step S14 of annealing the heater 40.

The annealing is to remove the processing effect and the thermal history remaining in an internal structure of a material by appropriately heating the metal material. The annealing is a kind of heat treatment method in which metal is heated to a predetermined temperature and then is gradually cooled so as to correct the internal deformation of the metal or the like, and is performed to lower the hardness and strength of the metal and improve formability, thus obtaining a certain structure. The annealing is the process of heating iron or steel to a proper temperature and slowly cooling the iron or steel so as to soften the iron or steel, adjust a crystalline structure or remove internal stress.

Thus, the residual stress of the heater 40 can be reduced or removed by annealing the heater 40.

After the step of forming the slit 100, the method may further include a step S20 of polishing the silicon substrate 10 and forming the through hole 110.

Although the present disclosure was described with reference to specific embodiments shown in the drawings, it is apparent to those skilled in the art that the present disclosure may be changed and modified in various ways without departing from the scope of the present disclosure, which is described in the following claims.

What is claimed is:

1. A contact combustion type hydrogen sensor, the sensor comprising:
   a substrate comprising silicon;
   lamination layers disposed over a top surface of the substrate, the lamination layers comprising a first thin oxide layer on the top surface of the substrate and a first thin nitride layer over a top surface of the first thin oxide layer;
   a heater disposed over the lamination layers, the heater comprising a connecting part electrically connected to a predetermined part and a heating part configured to be heated in response to power being applied;
   insulating layers covering a top surface of the heater, the insulating layers comprising a second thin oxide layer on the top surface of the heater and a second thin nitride layer on a top surface of the second thin oxide layer;
   a platinum catalyst having a shape of a circle over the insulating layers and configured to be heated by the heater to perform a hydrogen reaction;
   a slit outside the heating part and passing through the substrate and the lamination layers; and
   a through hole vertically penetrating through the substrate and the first thin oxide layer;
   wherein the heater is formed in a linear shape;
   wherein the heater comprises the connecting part on each of opposite ends of the heater electrically connected to the predetermined part, and the heating part on a middle portion of the heater;
   wherein the heating part is formed such that an outer portion of the heating part is formed in a shape of a circle and a pattern is formed inside the circle; and
   wherein the slit is formed in a circular shape on an outside to surround the shape of the circle of the heating part and the platinum catalyst.

2. The sensor of claim 1, wherein the slit further passes through the insulating layers.

3. The sensor of claim 1, further comprising:
   a through groove in each of the insulating layers to pass to the connecting part of the heater; and
   a metal pad inserted into the through groove and configured to input the power from an external device.

4. The sensor of claim 1, further comprising an etch line on each of the insulating layers extending along an outside of the heating part.

5. The sensor of claim 1, wherein the platinum catalyst is deposited on the heater through a MEMS batch process.

6. The sensor of claim 1, wherein the through hole is situated to allow heat generated from the heater to escape to a bottom of the through hole.

7. A method of manufacturing a contact combustion type hydrogen sensor, the method comprising:
   forming lamination layers on a substrate comprising silicon, the lamination layers comprising a first thin oxide layer and a first thin nitride layer;
   depositing and patterning a heater on the first thin nitride layer, the heater comprising a heating part and a connecting part;
   forming insulating layers on the heater, the insulating layers comprising a second thin oxide layer on the heater and a second thin nitride layer on the second thin oxide layer;
   depositing a platinum catalyst having a shape of a circle on the second thin nitride layer;
   forming a slit along an outside of the heating part; and
   forming a through hole after forming the slit, wherein the through hole vertically penetrates through the substrate and the first thin oxide layer;
   wherein the heater is formed in a linear shape;
   wherein the heater comprises the connecting part on each of opposite ends of the heater electrically connected to a predetermined part, and the heating part on a middle portion of the heater;
   wherein the heating part is formed such that an outer portion of the heating part is formed in a shape of a circle and a pattern is formed inside the circle; and
   wherein the slit is formed in a circular shape on an outside to surround the shape of the circle of the heating part and the platinum catalyst.

8. The method of claim 7, further comprising forming a through groove in the second thin oxide layer.

9. The method of claim 8, further comprising depositing a metal pad connected to the connecting part after forming the through groove.

10. The method of claim 7, further comprising annealing the heater after depositing the second thin oxide layer on the heater.

11. The method of claim 7, further comprising polishing the substrate.

12. A method of manufacturing a contact combustion type hydrogen sensor, the method comprising:
   forming a first thin oxide layer on a substrate;
   forming a first thin nitride layer on the first thin oxide layer;
   depositing and patterning a heater on the first thin nitride layer, the heater comprising a heating part and a connecting part;
   forming a second thin oxide layer on the heater;
   annealing the heater after forming the second thin oxide layer;
   forming a through groove in the second thin oxide layer to expose a top surface of the connecting part of the heater;
   depositing a metal pad in the through groove, wherein the metal pad is connected to the connecting part;
   forming a second thin nitride layer on the second thin oxide layer;
   depositing a platinum catalyst having a shape of a circle on the second thin nitride layer;
   forming a slit along an outside of the heating part, the slit passing through the substrate, the first thin oxide layer, and the first thin nitride layer; and
   forming a through hole after forming the slit, wherein the through hole vertically penetrates from through the substrate and the first thin oxide layer;
   wherein the heater is formed in a linear shape;
   wherein the heater comprises the connecting part on each of opposite ends of the heater electrically connected to a predetermined part, and the heating part on a middle portion of the heater;
   wherein the heating part is formed such that an outer portion of the heating part is formed in a shape of a circle and a pattern is formed inside the circle; and
   wherein the slit is formed in a circular shape on an outside to surround the shape of the circle of the heating part and the platinum catalyst.

13. The method of claim 12, wherein the substrate comprises silicon, the first thin oxide layer comprises $SiO_2$, and the first thin nitride layer comprises $Si_3N_4$.

14. The method of claim 12, wherein the slit further passes through the second thin oxide layer and the second thin nitride layer.

15. The method of claim 12, wherein depositing the platinum catalyst is performed using a MEMS batch process.

16. The method of claim 12, further comprising polishing the substrate.

17. The method of claim 12, further comprising marking etch lines on the second thin oxide layer and the second thin nitride layer, wherein the etch lines extend along the outside of the heating part, and wherein the slit is formed by etching along the etch lines.

* * * * *